(12) United States Patent
Mintchev et al.

(10) Patent No.: US 9,579,227 B2
(45) Date of Patent: Feb. 28, 2017

(54) INGESTIBLE IMPLEMENT FOR WEIGHT CONTROL

(71) Applicants: Martin Mintchev, Calgary (CA); Orly Yadid-Pecht, Haifa (IL); Michel Fattouche, Calgary (CA)

(72) Inventors: Martin Mintchev, Calgary (CA); Orly Yadid-Pecht, Haifa (IL); Michel Fattouche, Calgary (CA)

(73) Assignee: EAT LITTLE INC., Calgary, Alberta (CA)

( * ) Notice: Subject to any disclaimer, the term of this patent is extended or adjusted under 35 U.S.C. 154(b) by 1086 days.

(21) Appl. No.: 13/687,153

(22) Filed: Nov. 28, 2012

(65) Prior Publication Data

US 2014/0148840 A1   May 29, 2014

Related U.S. Application Data

(62) Division of application No. 12/294,659, filed as application No. PCT/CA2007/000512 on Mar. 29, 2007, now Pat. No. 8,389,003.

(Continued)

(51) Int. Cl.
*A61M 29/00*   (2006.01)
*A61F 5/00*    (2006.01)

(52) U.S. Cl.
CPC .................. *A61F 5/0073* (2013.01)

(58) Field of Classification Search
CPC . A61B 17/22; A61B 17/22031; A61B 17/221; A61B 2017/2215; A61B 2017/2217; A61F 5/0073
See application file for complete search history.

(56) References Cited

U.S. PATENT DOCUMENTS

| 4,485,805 A | 12/1984 | Foster, Jr. |
| 4,739,758 A | 4/1988 | Lai et al. |

(Continued)

FOREIGN PATENT DOCUMENTS

| WO | 2004056343 | 7/2004 |
| WO | 2006047882 | 5/2006 |

(Continued)

OTHER PUBLICATIONS

Van Bennekum, et al., Mechanisms of cholesterol-lowering effects of dietary insoluble fibres: relationship with intestinal and hepatic cholesterol parameters. Br J Nutr. 2005. pp. 331-337, vol. 94(3).

(Continued)

*Primary Examiner* — Gregory Anderson
*Assistant Examiner* — Sarah Simpson
(74) *Attorney, Agent, or Firm* — Kyle R. Satterthwaite; Ryan W. Dupuis; Ade & Company Inc.

(57) ABSTRACT

An orally administrable implement for expanding in a stomach of an animal, including a mammal, to fill a space in the stomach, is provided for weight control. The implement includes: a fluid-permeable expandable container having a first dimension and a second dimension; and a plurality of clusters comprising a swellable material contained within the container and capable of swelling when contacted with a fluid; whereby when the implement is ingested, the fluid in the stomach enters the container causing the clusters therein to swell and the container to expand from the first dimension to the second dimension.

24 Claims, 15 Drawing Sheets

Related U.S. Application Data

(60) Provisional application No. 60/743,883, filed on Mar. 29, 2006, provisional application No. 60/788,077, filed on Apr. 3, 2006, provisional application No. 60/838,324, filed on Aug. 18, 2006, provisional application No. 60/853,350, filed on Oct. 23, 2006, provisional application No. 60/875,194, filed on Dec. 18, 2006, provisional application No. 60/904,758, filed on Mar. 5, 2007.

(56) References Cited

U.S. PATENT DOCUMENTS

| | | |
|---|---|---|
| 4,899,747 A | 2/1990 | Garren et al. |
| 5,234,454 A | 8/1993 | Bangs |
| 5,750,585 A | 5/1998 | Park et al. |
| 5,993,473 A | 11/1999 | Chan et al. |
| 6,271,278 B1 | 8/2001 | Park et al. |
| 6,290,989 B1 * | 9/2001 | Asmussen ............. A61D 7/00 424/456 |
| 6,306,439 B1 | 10/2001 | Penners et al. |
| 6,449,511 B1 | 9/2002 | Mintchev et al. |
| 6,450,946 B1 | 9/2002 | Forsell |
| 6,453,907 B1 | 9/2002 | Forsell |
| 6,454,699 B1 | 9/2002 | Forsell |
| 6,460,543 B1 | 10/2002 | Forsell |
| 6,461,293 B1 | 10/2002 | Forsell |
| 6,535,764 B2 | 3/2003 | Imran et al. |
| 6,542,776 B1 | 4/2003 | Gordon et al. |
| 6,579,301 B1 | 6/2003 | Bales et al. |
| 6,600,953 B2 | 7/2003 | Flesler et al. |
| 6,606,523 B1 | 8/2003 | Jenkins |
| 6,615,084 B1 | 9/2003 | Cigaina |
| 6,684,104 B2 | 1/2004 | Gordon et al. |
| 7,066,945 B2 | 6/2006 | Hashiba et al. |
| 2003/0092673 A1 * | 5/2003 | Struszczyk ............. A23L 1/308 514/55 |
| 2004/0192582 A1 | 9/2004 | Burnett et al. |
| 2005/0228268 A1 | 10/2005 | Cole |
| 2006/0020278 A1 | 1/2006 | Burnett et al. |
| 2006/0155311 A1 | 7/2006 | Hashiba et al. |
| 2010/0215732 A1 * | 8/2010 | Mintchev ............. A61F 5/0036 424/451 |

FOREIGN PATENT DOCUMENTS

| | | |
|---|---|---|
| WO | 2006122019 | 11/2006 |
| WO | 2007017842 | 2/2007 |

OTHER PUBLICATIONS

Devaraj, S. and Jialal, I., The role of dietary supplementation with plant sterols and stanols in the prevention of cardiovascular disease. Nutr Rev. 2006. pp. 348-354, vol. 64(7).

Rodriguez, MS and Albertengo, LE., Interaction between chitosan and oil under stomach and duodenal digestive chemical conditions. Biosci Biotehnol Biochem. 2005. pp. 2057-2062, vol. 69(11).

"Biocompatible/biodegradable materials." (Tutorial) Sigma-Aldrich. 2005. http://www.sigmaaldrich.com/materials-science/biomaterials/tutorial.html.

* cited by examiner

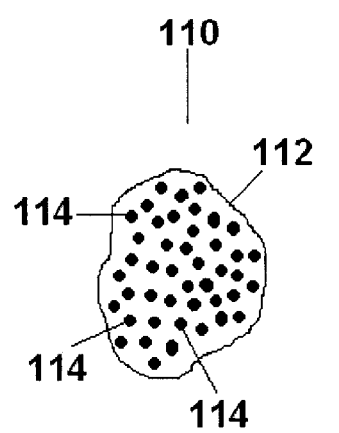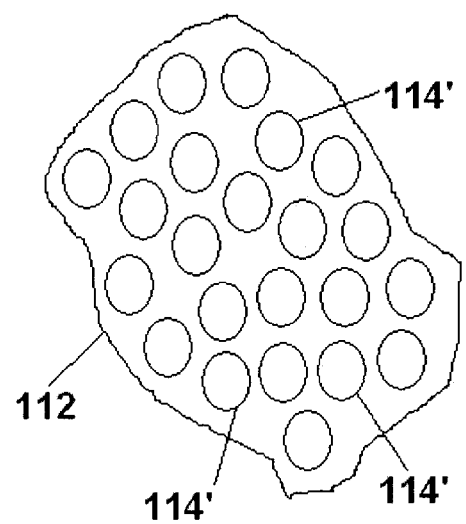
FIG. 3A
FIG. 3B

INGESTIBLE IMPLEMENT FOR WEIGHT CONTROL

CROSS REFERENCE TO RELATED APPLICATIONS

This application is a divisional application of U.S. application Ser. No. 12/294,659 filed Mar. 29, 2007, which is presently pending. U.S. Ser. No. 12/294,659 is a 371 of international application PCT/CA2007/000512 filed Mar. 29, 2007 which This application claims the benefit of U.S. Provisional Patent Application No. 60/743,883, filed Mar. 29, 2006; 60/788,077, filed Apr. 3, 2006; 60/838,324, filed Aug. 18, 2006; 60/853,350, filed Oct. 23, 2006; 60/875,194, filed Dec. 18, 2006; and 60/904,758, filed Mar. 9, 2007, all of which are incorporated herein by reference.

FIELD OF THE INVENTION

The present invention relates to the field of ingestible dosage forms, and, more specifically, to an orally administrable implement comprising expandable material useful for weight control and the treatment of obesity.

BACKGROUND OF THE INVENTION

Weight control and treatments for obesity have been the subjects of a large amount of suggested diets, treatments and procedures, including, in the most severe cases of morbid obesity, device implantations and/or direct surgical interventions. Recent comprehensive statistics from the National Institutes of Health (USA) indicates that more that 40% of Americans are obese, with more than 20% of these individuals being morbidly obese. In addition, it can be estimated that at least twice as many people are seeking to control their body weight, and/or are adhering to diets or other weight-control mechanisms. This is particularly significant since obesity has been implicated as a leading cause of various clinical conditions, including cardiovascular diseases and diabetes.

Six major streams of research and development related to new treatments for obesity are currently available: (1) diet regiments, and diet-related supplements and treatments; (2) pharmacological treatment using specifically developed medications; (3) gastric stimulation using implantable electronic devices; (4) invasive surgical procedures related to gastric reduction; (5) intragastric balloons or bezoars for reducing gastric volume and introducing a sensation of satiety and fullness; and (6) oral administration of cellulose or polymeric-based substances, which expand in the stomach and preclude their expulsion through the pylorus with the process of natural gastric peristalsis, thus introducing sensation of fullness and satiety. These expanded polymeric substances subsequently disintegrate chemically to allow for their expulsion from the body with natural gastrointestinal peristalsis.

Currently, there are very large numbers of various diets, diet supplements, diet regimens, and combinations thereof, and their numbers are growing dramatically. However, in many cases, these weight loss strategies do not work, or their success is very limited. The success of these techniques often varies widely between individuals, and they are often not sustainable.

Weight-loss related pharmacological treatment based on specifically developed and clinically-tested drugs and/or health supplements has also not been very successful. Numerous such therapies have been associated with various side effects, some of which are quite serious and life-threatening. Therefore, commercially-available and clinically-proven diets and/or anti-obesity drugs and health supplements have yet to be developed.

Recently developed techniques for gastric stimulation (see for examples U.S. Pat. Nos. 6,684,104, 6,615,084, 6,606,523, 6,600,953, 6,542,776, 6,535,764, and 6,449,511), involving surgical implantation of miniature microelectronic devices have been proposed as an avenue to tackle more severe cases of obesity, and particularly morbid obesity. The devices can administer electrical signals to the stomach and adversely affect normal propulsive gastric peristalsis. However, the procedures used for the positioning of the stimulating electrodes as well as the implantation of the device remain invasive, and the long-term effect of the treatment remains unknown both in terms of sustainability and safety.

Surgical procedures related to gastric volume reduction are invasive measures to address the problem of obesity. Mortality rates of procedures like gastric bypass or direct gastric volume reduction can reach 2%, have prolonged recovery periods, and can be quite expensive.

Intragastric balloons or bezoars positioned in the stomach either surgically or endoscopically to reduce the effective gastric volume have been found effective in introducing early satiety and sensation of fullness, thus contributing to reduced food intake, which has been reliably related to sustainable weight loss (see for example U.S. Pat. Nos. 4,739,758, 4,485,805, 4,899,747, 5,234,454, 5,993,473, and 6,579,301). More recently, wireless control of volume-controlling devices in the stomach has been suggested (see for example U.S. Pat. Nos. 6,461,293, 6,454,699, 6,453,907, 6,460,543, and 6,450,946). Most recently, a "bow-tie" or "butterfly" intragastric bezoar has been suggested (WO/2006/122019, U.S. Patent Application No. 20060155311, U.S. Pat. No. 7,066,945) in contrast with the balloon shape proposed previously. The latter is launched endoscopically in the stomach and it is subsequently removed also invasively.

All these techniques remain invasive and can be associated with serious and sometimes life-threatening side effects. The bezoars are positioned and removed invasively (in most cases endoscopically), and, being built from non-permeable, impervious materials, and not being disintegratable within the gastrointestinal tract, they can potentially create life-threatening obstructions in the intestines, if they accidentally deflate, reduce volume or otherwise malfunction in the stomach and exit through the pylorus. These devices are not autonomously expandable and disintegratable from within the gastric lumen, and therefore are positionable and removable invasively (predominantly endoscopically). In addition, the lack of control over the dimensions of these bezoars triggers numerous other side effects in substantial number of patients, including vomiting, hypokalemia, abdominal pain, functional renal pain, gastroesophageal reflux, etc.

Most recently, the use of swellable polymers has been proposed to facilitate the reduction of gastric volume for treating obesity (see for example U.S. Pat. Nos. 5,750,585, 6,271,278, German Pat. No. NDN-050003290517, US Patent Application No. 20040192582, US Patent Application No. 20060020278). Compressed cellulose derivatives, or dehydrated hydrophilic polymers are introduced orally in the stomach, and expand to the point of not being able to pass through the pylorus, thus effectively achieving non-invasively what an intragastric balloon or another gastric volume-reducing device would achieve. However, the subsequent decomposition and/or degradation of these polymers to allow for expulsion through natural peristalsis can be very problematic. More specifically, the decomposition and/or degradation rate is not precisely controlled, and the volume and the number of the decomposing/degrading parts or portions is unknown. More importantly, since this decomposition is pharmacologically-based and takes place simultaneously on different number of parts or portions, its timing cannot be precisely controlled since it would depend on numerous external factors related to the gastric pH, enzyme content, peristaltic pattern, and the anatomy of the particular patient. Because of the uncontrolled nature of the polymer decomposition, it is possible that the volume of the stomach may remain in an expanded state for long intervals of time, which can lead to serious side effects and significant discomfort. Moreover, improper decomposition and/or degradation may lead to serious complications such as small bowel obstructions. In addition, this makes designing an appropriate diet using this technique difficult, if not impossible.

Consequently, the need has arisen for non-invasive techniques or products that can be easily used for prolonged and controlled reduction of gastric volume for use in facilitating weight loss, which address some of the problems encountered in the prior art.

SUMMARY OF THE INVENTION

According to a broad aspect of this invention, there is provided an orally administrable implement for expanding in a stomach of an animal, including a mammal, to fill a space in the stomach, the implement including:
 a fluid-permeable expandable container having a first dimension and a second dimension; and
 a plurality of clusters comprising a swellable material contained within the container and capable of swelling when contacted with a fluid;
whereby when the implement is ingested, the fluid in the stomach enters the container causing the clusters therein to swell and the container to expand from the first dimension to the second dimension.

Preferably, the implement can be self-administrable (in the case of humans) or administrable autonomously or unaided, meaning the implement is administrable without the need of any external positioning or manipulating device functionally attached to it, such as an endoscope.

Preferable, when the container has the first dimension, the implement can be retained in a capsule capable of being easily swallowed or administered autonomously. Once the capsule has dissolved and the container is released in the stomach, the gastric fluids will enter the fluid-permeable expandable container. When the fluid contacts the clusters, the clusters will swell and the container will expand to the second dimension. When the container has expanded to the second dimension, it is sufficiently large so as to be retained in the stomach. The capsule can be any gelatin capsule known in the art, for example, a pH-sensitive AAA capsule made from Capsugel™, Greenwood, S.C., which disintegrates rapidly in the stomach but not in the esophagus.

In one embodiment, the container is biodegradable over time. Thus, when the implement is in the stomach, the stomach fluids will cause the container to biodegrade, thereby releasing the swelled clusters from the container and into the stomach. In a preferred embodiment, the clusters swell to a size that does not exceed 1 cm in diameter and therefore each cluster can readily exit the stomach through the pylorus. Preferably, the clusters swell to a size not exceeding about 0.5 cm to about 0.6 cm. In one embodiment, the clusters cannot fuse into each other either when dry or when swelled. In another embodiment, the clusters can be pre-fused when dry, to form a homogeneous structure when they swell. However, the said structure remains porous and fluid-permeable, and can be taken apart by gastric peristaltic forces after the container biodegrades.

In one embodiment, the container is made of specific biodegradable woven, knitted, braided or monofilament mesh material, such as Vicryl™ (Ethicon), Monosyn™ (B Braun), catgut, and the like, which allows fluid to permeate. In another embodiment, the container is made from a biodegradable fluid-permeable stretchable material such as interlaced regenerated oxidized cellulose (for example, Curacel™ by CuraMedical By, Amsterdam, Holland), which expands or stretches from the first dimension to the second dimension when the clusters swell.

In another embodiment, the container comprises a plurality of smaller sections, whereby each section is attached to one another by biodegradable fibers to form the container. The biodegradable fibers can be made of an absorbable biocompatible material, which can include, but is not limited to, polycaprolactone, polyglycolide, polylactide, or combinations thereof (commercially available under the names Selecture PLL™ and Selecture VEH™ by Schering-Plough Animal Health Corporation). The biodegradable fibers can further be made, for example, from any absorbable suture known in the art such as Vicryl™, Monosyn™, catgut, PDS II™ (Ethicon, Cornelia, Ga.), or any other appropriate braided or monofilament absorbable suture. Soft monofilament material or material such as regenerated oxidized cellulose (for example, Curacel) or catgut could be utilized also to avoid possible mucosal injuries.

In another embodiment, the container is made from permeable biodegradable mesh such as Vicryl™ Knitted Mesh by Ethicon, Curacel™ by CuraMedical, or Safil™ Mesh by B Braun and the mesh has radial fibers made, for example, from absorbable surgical suture such as Vicryl™, PDS II™ (Ethicon), catgut, regenerated cellulose or Monosyn™ (B Braun) woven therethrough. The radial fibers are biodegradable, hence when the fibers begin to disintegrate the volume of the container collapses, the container loses its integrity due to the gastric peristaltic forces, and the clusters are released.

In one embodiment, the clusters comprise a swellable material selected from the group consisting of a swelling bentonite, microcrystalline hydrogels, polyolefins and various mixtures thereof. Other swellable materials that could be used include, by are not limited to, other natural clays, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. Furthermore, if desired, the clusters comprise a swellable material that is also biodegradable, thereby further facilitating each clusters passage through the intestines. It is understood that a variety of other biocompatible super-absorbent polymers known in the art can be used to form the clusters of the present invention, for example, polymers of poly(2-hydroxyethyl methacrylate) by Aldrich, Milwaukee, Wis., or of polyacrylamide, or of an appropriately cross-linked poly (acrylic acid) (for example, one produced by Wako Pure Chemical Industries, Japan) which expand adequately in low pH environment, but lose volume at higher pH environment (above 6).

In one embodiment, the orally administrable implement further comprises a magnet retained in the container, for example, a spherical rare Earth magnet covered by a thin biocompatible silicone cover. Thus, when two or more orally administrable implements are ingested, the magnets can attract one another and form a complex of implements. Other means for concatenating more temporary bezoars post-ingestion into a single mass may be used, which may include miniature permanent magnets or Velcro or any kind of fastener.

The orally administrable implement of the present invention may also further include at least one active agent, which can be releasably associated with either the container, the clusters of swellable molecules, or both. The active agent might also be independently included in the container together with the clusters comprising a swellable material. The active agent may be selected from a wide group of agents, which include, but are not limited to, enzymatic agents, medicinal agents, chemical agents, or combinations thereof. For example, which is not meant to be limiting, the bezoar platform created by the implement can be used for the slow release of vitamins, minerals, glucose containing substances, medication, etc. These substances can be impregnated to the container, the swellable clusters, or both. Alternatively, they can be included independently in the container together with the swellable polymer clusters.

In one embodiment, the implement may include a plurality of clusters comprising a substance-absorbing material (for example, but not limited to, lipid-absorbing clusters) contained within the container and capable of absorbing targeted substances present in the gastric fluid. For example, which is not meant to be limiting, the substance-absorbing clusters may be lipid-absorbing and may comprise chitosan, or any other material known to have lipid-absorbing properties. The substance-absorbing clusters will be retained in the stomach for a sufficiently long period of time, which will allow the substance-absorbing clusters to absorb targeted substance or substances in the stomach, thereby reducing the content of these targeted substances in the ingested food before their absorption in the intestines. Similar to the clusters comprising a swellable material, upon the disintegration of the container, the substance-absorbing clusters can exit the gastrointestinal tract without creating any obstruction, and without releasing the absorbed substance or substances to be absorbed by the body. Furthermore, on their way to exiting the body the said substance-absorbing clusters can continue absorbing targeted substances in other gastrointestinal organs distal to the stomach. Thus, the amount of targeted substances absorbed by the body can be substantially reduced, modified, or manipulated.

Clusters comprising a substance-absorbing material (for example, lipid-absorbing clusters) can include any material that is capable of absorbing targeted substances from the ingested food chime, and can include, but are not limited to, to include cholestyramine, chitosan, cellulose, plant sterols and stanols. The synthesis of such absorbent molecules have been previously described in the following references, incorporated herein by reference: (1) Van Bennekum et al., Br J. Nutr. 2005 September 94(3):331-7); (2) Devaraj S and Jialal I, *Nutr Rev.* (2006 July) 64(7 Pt 1): 348-54; (3) Rodriguez Miss. and Albertengo L E, *Biosci Biotechnol Biochem* (2005 November) 69(11): 2057-62.

In another embodiment, the implement may include a container made from fibers comprising a substance-absorbing material (for example, but not limited to, lipid-absorbing chitosan fiber, or oxidized cellulose fiber) capable of absorbing targeted substances present in the gastric fluid. For example, which is not meant to be limiting, the substance-absorbing fibers utilized to make the container may be lipid-absorbing and may comprise chitosan, oxidized regenerated cellulose, or any other material known to have lipid-absorbing properties. The container will be retained in the stomach for a sufficiently long period of time, which will allow it to absorb targeted substance or substances in the stomach, thereby reducing the content of these targeted substances in the ingested food before their absorption in the intestines. Upon the disintegration of the container, the substance-absorbing fibers can exit the gastrointestinal tract without creating any obstruction, and without releasing the absorbed substance or substances to be absorbed by the body. Furthermore, on their way to exiting the body the said fibers can continue absorbing targeted substances in other gastrointestinal organs distal to the stomach. Thus, the amount of targeted substances absorbed by the body can be substantially reduced, modified, or manipulated.

Containers can be made from a substance-absorbing fiber (for example, lipid-absorbing fiber) that can include any material that is capable of absorbing targeted substances from the ingested food chime, and can include, but are not limited to, chitosan and cellulose.

According to another broad aspect of this invention, there is provided an orally administrable implement for expanding in a stomach of an animal, including a mammal, to fill a space in the stomach, the implement including:
  a carrier;
  at least one fluid-permeable expandable container having a first dimension and a second dimension;
  a plurality of clusters comprising a swellable material contained within each container and capable of swelling when contacted with a fluid; and
  a coupler for coupling the at least one expandable container to the carrier;
whereby when the implement is ingested, the fluid in the stomach enters the container causing the clusters therein to swell and the container to expand from the first dimension to the second dimension.

Preferably, the implement can be self-administrable (in the case of humans) or administrable autonomously or unaided, without the need of any external positioning or manipulating device functionally attached to it, such as an endoscope.

In one embodiment, when the at least one container has the first dimension, the orally administrable implement can be retained in a capsule capable of being easily swallowed. The capsule can be any gelatin capsule known in the art, for example, a pH-sensitive AAA capsule made from Capsugel™, Greenwood, S.C., which disintegrates rapidly in the stomach but not in the esophagus. Once the capsule disintegrates, gastric fluid will be able to enter the at least one container and the clusters comprising a swellable material will swell. The swelled clusters will cause the at least one container to expand to the second dimension. The implement will then be of a sufficiently large size so as to be retained in the stomach.

In one embodiment, the coupler comprises a piece of absorbable biodegradable surgical suture for releasably attaching the container to the carrier. In another embodiment, the coupler is a piece of biodegradable medical gauze. In one embodiment, the container has an open end which is tied closed with one end of the absorbable surgical suture or medical gauze and the other end of the absorbable surgical suture or medical gauze is attached to the carrier. Thus, when the suture or gauze biodegrades, the container is opened and the swelled clusters are expelled into the stomach. It is understood that other couplers can be used, for example, any biocompatible glue.

In one embodiment, the implement may further include a plurality of clusters comprising a substance-absorbing material (for example, but not limited to, lipid-absorbing clusters) contained within the container and capable of absorbing targeted substance or substances present in the gastric fluid.

In another embodiment, the implement may further include at least one container made from a substance-absorbing fiber (for example, but not limited to, lipid-absorbing fiber) capable of absorbing targeted substance or substances present in the gastric fluid or in the fluids of other gastrointestinal organs distal to the stomach.

In another broad aspect of the present invention, a built-in microelectronic system can be provided to inform the user about the exact moment the clusters are released from the containers, or when the containers are released from the carrier, or both. For example, an internal radio-frequency (RF) transmitter or RF identification tag (RFID) can be provided so that subsequent dosage of this anti-obesity treatment can be more precisely timed. Thus, the obtained reduction of gastric volume can be systematically and consistently monitored and maintained for a pre-determined therapy duration by periodically re-administering one or more implements after information has been obtained that a given ingested implement or implements has/have disintegrated. The microelectronic system monitoring the disintegration and the miniature RF transmitter may be both operably associated with the carrier, or the container, or both.

In one embodiment, the microelectronic system monitoring the disintegration and the miniature RF transmitter or RFID tag are operably associated with the carrier. In one embodiment, the carrier has an outer surface and an inner surface and the inner surface forms an internal cavity. In this embodiment, the internal cavity may be used to house the microelectronic system and the RF transmitter or the RFID tag. In a further embodiment, the microelectronic system may further comprise a battery that may also be housed in the internal cavity of the carrier. In yet another embodiment, the RFID tag or the RF transmitter can be used to track and locate the animal, including a mammal that has ingested the implement.

The carrier may adopt a wide variety of different shapes, which can include, but are not limited to, sphere, pyramid, cylinder and cube shapes or combinations thereof. The carrier can be external or internal to a container.

According to another broad aspect of this invention, there is provided an orally administrable dosage form, the dosage form comprising: one or more orally administrable implements and at least one pharmaceutically acceptable excipient. The dosage form may be a capsule, which can be coated with a pH-sensitive coating layer. The pH-sensitive coating layer can be formulated to prevent dissolution prior to the dosage form reaching the stomach.

According to another broad aspect of this invention, there is provided a method for the non-invasive reduction of gastric volume, the method comprising the steps of: (a) orally administering at least one orally administrable implement as described above; (b) contacting the orally administrable implement with gastric juice to allow for the clusters to expand and prevent the orally administrable implement from exiting the stomach; (c) after a desired period of time, releasing the clusters from the orally administrable implement so that the clusters may exit from the stomach; and (d) maintaining the reduced gastric volume for a pre-determined therapy duration by systematically and periodically ingesting additional orally administrable implements once some of the already ingested implements have disintegrated.

According to another broad aspect of this invention, there is provided a schedule for the administration of the implement (also referred to herein as an ingestible temporary bezoar), so that the therapy becomes part of a weight-reduction diet leading to behavioral and lifestyle modifications needed to sustain weight loss for a substantial period of time after the therapy is discontinued. This schedule includes, but is not limited to, maintaining an active therapy with expanded temporary bezoars in the stomach for 2-3 months, during which period it is combined by an appropriately designed diet, which facilitates the said behavioral and lifestyle modifications. Subsequently, the temporary bezoars disintegrate and leave the body naturally, but the behavioral and lifestyle modifications remain in place for a substantial post-therapy period. The administration of the ingestible capsule can be, but is not limited to, immediate; daily; weekly; monthly. These administration schedules are illustrated below by the means of example of bezoars lasting in the stomach for 80 days, which is used for illustrative purposes only. Bezoars can last in the stomach a wide range of days, for example, which is not meant to be limiting, from 1 to 120 days.

Immediate administration of the capsules can take place in one single day after the necessary patient-specific gastric volume reduction has been determined. For example, if an implement contained in a single capsule swells in the stomach to a 50 cc temporary bezoar, and during the assessment of the gastric volume of a particular patient it has been determined, that a 500 cc volume reduction of the stomach would be beneficial for this patient, 10 capsules will be administered in a sequence within a short interval of time, and with abundant amount of water (at least 1000 ml). Following the administration, the desired gastric volume reduction will be achieved immediately after the last capsule has been ingested, and after a predetermined number of days (for example, which is not meant to be limiting, 80 days), the disintegration of the bezoars will start occurring, clearing the stomach from the bezoars in a relatively short period of time.

In the case of daily administration, the patient ingests a single capsule every day with a sufficient amount of water (for example, 500 ml per capsule). The numbers of days in which capsules are ingested depend on the desired volume that the swollen bezoars should take in the stomach. For example, if an implement contained in a single capsule swells in the stomach to a 50 cc temporary bezoar, and during the assessment of the gastric volume of a particular patient it has been determined, that a 500 cc volume reduction of the stomach would be beneficial for this patient, one capsule is administered every day for 10 days. Then, the prescribed gastric volume reduction is achieved in 10 days. From the $11^{th}$ day after the start of the administration of the capsules, the said therapy is completely functional, until the earliest administered temporary bezoar starts disintegrating, for example at $80^{th}$ day of the start of the therapy.

In an alternative example of weekly administration, the therapy is ongoing, with a single capsule being administered every week for 20 weeks, i.e., during the duration of the entire therapy. Thus, maximal volume of the temporary gastric bezoars is achieved at week 10. At week 11, the bezoar ingested at week 1 will start disintegrating, and is replaced by the newly ingested device in the given week.

In the example of monthly administration, the therapy is ongoing, with a single capsule being administered every month indefinitely. Thus, maximal volume of the temporary gastric bezoars is achieved at month 3. At month 4, the temporary bezoar ingested at month 1 will start disintegrating, and is replaced by the newly ingested implement in the given month. So the steady state number of temporary bezoars inside the stomach is 3. This monthly therapy is useful for the long-term reduction of calorie intake.

The orally administrable implements of the present invention are preferably encapsulated in a dissolvable capsule known in the art. As soon as the encapsulated implement is ingested, the capsule starts disintegrating. The time of disintegration of the capsule needs to be long enough so that the capsule is not disintegrated fully prior to reaching the stomach but short enough so that the implement is not expelled though the pylorus prior to having the swellable clusters expanded fully through contact with aqueous solutions, such as gastric juices, so that the temporary bezoar attains new volume (called effective post-ingestion volume, the occupying volume of the temporary bezoar when fully expanded) that is much bigger than when it was contained in the ingestible capsule. The final effective post-ingestion volume of the pseudo-bezoar is generally 10 to 100 times larger than the volume of the pre-ingestion capsule encapsulating the dry temporary bezoar.

The implements of the present invention affect satiety by reducing gastric volume from inside of the stomach through the full expansion of the molecule clusters inside the volume contained by the permeable fiber-containing container. Preferably, the fully expanded or swelled clusters are contained within the container remain inside the stomach for a predetermined period of time. The container may or may not include coupling members for attachment to a carrier to help maintaining its volume during the contractile activity in the gastrointestinal tract. A plurality of containers can be attached to the carrier. After the predetermined period of time, the integrity of the container begins to be compromised, for example, the container may start to disintegrate, and the swelled clusters are let loose in the stomach. Alternatively, the container may comprise a plurality of individual sections which are attached to each other by means such as biodegradable fibers, disintegrating sutures, or the like, which when degrade or disintegrate cause the volume of the container to collapse. The sizes of the disintegrating or disintegrated container, the carrier, the coupling members, and the swelled clusters are such that individually they do not create obstruction anywhere in the gastrointestinal tract and all particles resulting from the disintegration are safely expelled through the GI tract.

In addition, there are provided optimization and safety measures for the implements of the present invention. The optimization measures can include, but are not limited to, one or more of the following:

i. Designing the container in such way that it is permeable to liquid and gaseous gastrointestinal content regardless of whether it is in assembled or disintegrated state;

ii. Designing the container in such way that it is of limited expanded volume (for example, a preferred embodiment of 50 cubic centimeters);

iii. Designing the container so that it disintegrates into smaller parts which individually can pass through the gut without creating any obstruction;

iv. Designing the container so that when containing a magnet in order to concatenate with another such container post ingestion, the new concatenated implement maintains its permeability to gastrointestinal liquid and gas, and upon disintegration of the respective containers the attached magnets are of such volume that can exit the gastrointestinal tract while remaining bonded together.

v. The implement uses such materials, which do not injure the mucosa in the gastrointestinal tract before or after disintegration.

vi. Designing the implement in such manner that it fits precisely in the volume of a standard ingestible capsule, without any unutilized space in the said capsule when closed;

vii. The biocompatible implement comprises a permeable container, clusters of biocompatible material expandable or swellable in aqueous solution such as gastric juice contained in the volume of the container, and the means for disintegrating the carrier so that the entire implement disintegrates into smaller pieces after a predetermined time in the stomach of an animal, including mammal. This disintegration is either intrinsic feature of the material used to design the container, or is facilitated by an external substance (in a preferred embodiment this could be a specific volume of Coca-Cola or Coca-Cola-like drink administered over a specific period of time), or both. The disintegration can typically occur between the first and the $120^{th}$ day post-ingestion.

viii. The safety measures can be of a wide variety, which can include, but are not limited to, designing the temporary bezoar in such way that it would pass gastrointestinal liquids of particular consistency while retaining its volume characteristics, segmenting the container into smaller parts or sections, kept together biodegradable material with shorter biodegradation lifespan than the container itself, or by using a material which is slowly disintegratable in gastric juice, but is rapidly disintegratable in the small intestine, so that intestinal obstruction is prevented. If needed, the pH in the stomach can be maintained at a value providing slow disintegration and maximal swelling of the clusters using an appropriate medication. For example, acid reduction therapy using omeprazole (0.5 mg/kg daily) can maintain the pH value in the stomach between 4 and 5 rather than the normal value of 2, without any side effect for the duration of the therapy, or for the duration of the initial expansion of the temporary bezoar, until it reaches its final effective post-ingestion volume. As mentioned, the speed of disintegration can be facilitated by administering external substance either transorally or transnasally.

ix. Further, the safety measures include, but are not limited to, selecting a material for the container that does not injure or inflame the mucosa of the gastrointestinal tract prior to or after the device disintegration, and selecting polymer clusters that (a) do not expand above 0.5 cm in diameter but cannot exit the carrier in unexpanded or expanded state until the carrier disintegrates; and (b) are made of substance that allow them to expand maximally in the stomach (pH 1-4) and in the presence of various and variable gastric enzymes, salts, and substances normally present in the stomach, but have substantially reduced expansion properties at higher pH ($>6$).

In addition, there are provided patient-specific administration schedules for the device, which administration schedules may include, but are not limited to, any one of the following:

i. Swallowing ingestible capsules, each capsule comprising an implement of the present invention, and each forming an artificial limited-volume temporary bezoar in the stomach in such way that the combined volume taken by these temporary gastric bezoars is specifically tailored to the gastric volume of the patients before the administration, so that the therapy does not modify the anatomy of the stomach when discontinued.

ii. The implement of the present invention may or may not contain a miniature RFID tag to identify its position in the GI tract. Through the use of the external RFID reader, the RFID is tracked and the device is judged to have moved out of the stomach.

iii. The means for disintegrating the container can be related to the material of the carrier itself, or can be controlled by a coupling member maintaining the integrity of the container until a predetermined moment in time.

iv. The patient-specific administration schedule includes, but is not limited to, preliminary assessment of the gastric volume of the patient using barostat measurement, barium X-ray measurement, scintigraphy, fluoroscopy, or any other objective technique for assessing gastric volume, and sequentially or simultaneously administering a number of capsules which form temporary bezoars of limited and pre-determined volume in the stomach, so that a known composite bezoar volume is obtained after all implements contained in the capsules expand, in such manner that the therapy is effective, but the stomach of the patient is not unnecessarily subjected to abnormal volume changes and stretching. Thus, each implement expands into the stomach to a limited volume, for example, 50 cubic centimeters, and various composite bezoar volumes can be obtained, e.g., 200 cc with 4 capsules (for smaller stomachs and children), 500 cc with 10 capsules (for larger stomachs), etc.

The implement of the present invention should preferably be of a shape, for example, but not limited to, a pillow-like shape, that will prevent the implement from exiting the stomach prematurely through the pylorus and create intestinal obstruction.

According to another broad aspect of the present invention, there is provided an orally-administrable pharmaceutical dosage form including at least one orally administrable implement of the present invention and, if desired, a pharmaceutically acceptable excipient such as binders, fillers and disintegrants, for example, starch. The pharmaceutical dosage form may take various forms, which include, but are not limited to, liquids, soft substances, powder-like substances, and hard pharmaceutical substances such as soft capsules, hard capsules and tablets. In one embodiment, the pharmaceutical dosage form is a capsule. In another embodiment, the capsule can be coated with a pH-sensitive coating. The pH-sensitive coating may prevent dissolution until the stomach reached, to prevent contact between the swellable clusters and aqueous solutions.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The present invention, both as to its organization and manner of operation, may best be understood by reference to the following description, and the accompanying drawings of various embodiments wherein like reference numerals are used throughout the several views, and in which:

FIG. 3A is a schematic view of another embodiment of an orally administrable implement according to the invention, where the container is in the first dimension.

FIG. 3B is a schematic view of the orally administrable implement of FIG. 3A in the expanded second dimension.

DESCRIPTION OF THE PREFERRED EMBODIMENTS

One embodiment of an orally administrable implement for expanding in a stomach of a animal, including mammal to fill a space in the stomach of the present invention includes a fluid-permeable expandable container having a first dimension and a second dimension; and a plurality of clusters comprising a swellable material contained within the container and capable of swelling when contacted with a fluid. When the swellable clusters contact the fluid in the stomach, the swellable clusters swell and the container expands from the first dimension, which is generally of a size that allows the implement to fit in a capsule, to the second dimension, which is generally of a size that passage of the implement through the pylorus is prevented, which can result in the attainment of a sensation of satiety for a specified period of time when the stomach remains filled with the implement.

After a desired amount of time has passed, the integrity of the container is compromised in a timed fashion, for example, by the disintegration of the container, and the swelled clusters are released from the container. This disintegration can allow the disintegrated parts of the container and the swelled clusters to now pass through the pylorus, and empty from the stomach. Preferably, each expanded or swelled cluster does not exceed 1 cm in diameter. When the said clusters are released from the container, they can individually pass through the pylorus.

The form of container can vary widely and disintegration of the container can be due to the container comprising a biodegradable material or comprising a plurality of sections held together by biodegradable materials such as fibers, absorbable surgical sutures or absorbable gauze. The actually timing of the disintegration of the container can be estimated by knowing the reduction in the tensile strength of the biodegradable fibers or gauze used to hold the sections of the container together after ingestion. This can be particularly useful for the facilitation of weight loss and the treatment of obesity. Thus, the orally administrable implement of the present invention can be a non-invasive treatment for obesity that can be timed, which can result in less discomfort to the subject ingesting the implement and the ability to design a specific diet plan utilizing this technology.

Figure 1A:
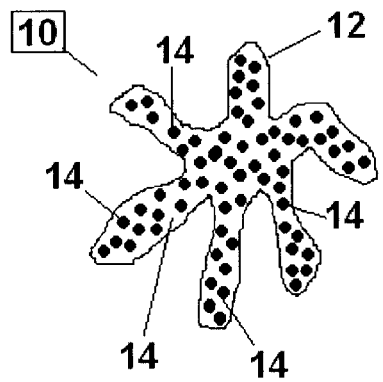
FIG. 1A is a schematic view of one embodiment of an orally administrable implement according to the invention, where the container is in the first dimension and the swellable clusters are unswelled.
Figure 1B:
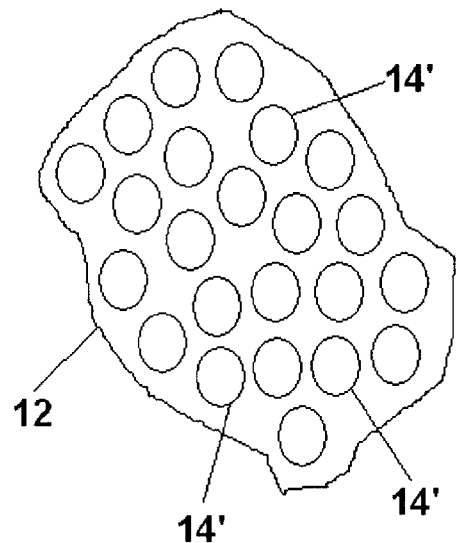
FIG. 1B is a schematic view of the orally administrable implement of FIG. 1A in the expanded second dimension as a result of the swellable clusters swelling.
Figure 1C:
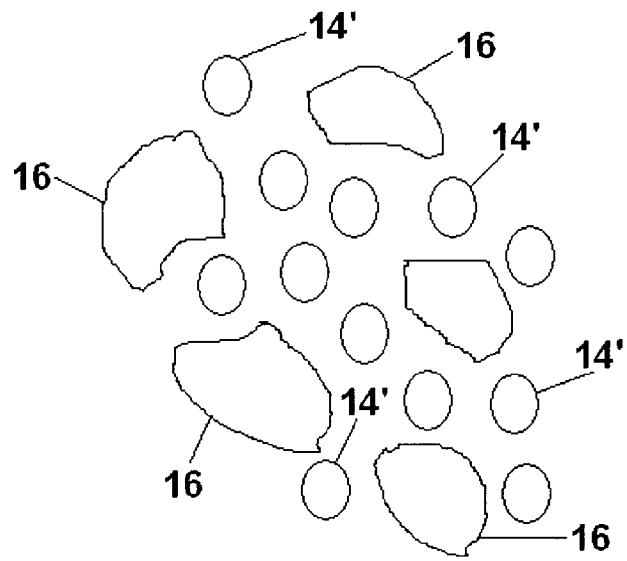
FIG. 1C is a schematic view of the orally administrable implement of FIG. 1B where the container is made of a biodegradable material for release of the swelled swellable clusters.

In one embodiment of the present invention, illustrated in FIGS. 1A, 1B and 1C, the orally administrable implement, referred to generally as 10, comprises a container 12, shown here in a folded, compact, first dimension. In this embodiment, container 12 is made from a biodegradable material that allows for the passage of fluid into its interior 13, for example, a permeable biodegradable mesh such as Vicryl™ Knitted Mesh by Ethicon, Curacel™ by CuraMedical, or Safil™ Mesh by B Braun. Further contained in the interior 13 of container 12 is a plurality of clusters 14 comprising a swellable material, whereby each swellable cluster is capable of swelling when contacted with fluid such as gastric fluid found in the stomach. For example, clusters 14 can comprise Aquagel™ by Akina Inc., West Lafayette, Ind. In FIG. 1A, the swellable clusters 14 are shown prior to contact with fluid, i.e., in their non-swelled form.

FIG. 1B shows implement 10 of FIG. 1A in its expanded form, after it has been delivered into the stomach and gastric fluid has been allowed to contact it. Container 12 is now shown in its second, expanded dimension, such that the implement 10 can no longer exit the stomach through the pylorus. The swellable clusters 14' are now shown in their swelled state due to the gastric fluid seeping through the container 12. The swelling of clusters 14' then causes container 12 to expand to the second dimension. Preferably, the swelled clusters 14' become spherical bodies not exceeding about 1 cm in diameter. The swellable clusters can be made of various substances, for example, appropriately cross-linked poly(acrylic acid) or poly(2-hydroxyethyl methacrylate). Preferably, they are of size not permitting their exit from the carrier when dry, and preferably not exceeding about 0.5 to about 0.6 cm when swollen in gastric fluid. In addition, preferably, they cannot grow any bigger in the small intestine and the colon to prevent them causing intestinal obstruction.

FIG. 1C represents the released pieces 16 of the container 12 in FIG. 1B once the container biodegrades, each piece 16 of which is of size precluding the possibility of creating obstruction in the small intestine. The container pieces 16 along with the swelled clusters 14' are released in the stomach, so that they can be propelled out of the body by natural peristalsis in a harmless fashion.

Figure 2:
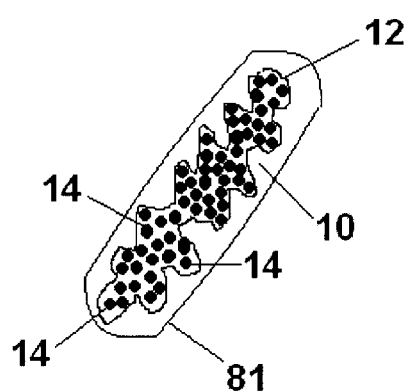
FIG. 2 is a schematic view of the orally administrable implement of FIG. 1A encapsulated in a capsule of the present invention.

FIG. 2 shows implement 10 of FIG. 1A contained within a shell 81, with container 12 holding the dry swellable clusters 14 in a folded conformation (first dimension) to facilitate oral administration. Shell 81 can be made of a variety of different materials, which can include, but are not limited to, pH-sensitive materials that will only dissolve under certain conditions, for example, the pH of the stomach. The material used to make the shell can be the same material, for example, gelatine or cellulose, used to make pharmaceutical capsules known in the art. Various sizes of shells can be used, as long as they are swallowable by the patient.

FIG. 3A is another embodiment of an orally administrable implement of the present invention, referred to generally as 110, comprising a container 112, shown here in a smaller first dimension, housing a plurality of clusters 114 comprising a swellable material shown here in the unswelled state. In this embodiment, container 112 is made from a fluid-permeable stretchable material such as regenerated oxidized cellulose (for example, Curacel™ by CuraMedical BV, Amsterdam, Holland) which expands or stretches from the first dimension to a second dimension, as shown in FIG. 3B, when the swellable clusters swell (clusters 114' in FIG. 3B). Regenerated oxidized cellulose fibers such as the ones utilized to make the container may or may not have substance-absorbing properties as well. For example, the oxidized cellulose fibers utilized to make the container can be fibers of the type M.doc™ (Micro Dispersed Oxidised Cellulose) manufactured by Alltracel Pharmaceuticals, Dublin, Ireland, which have proven lipid-absorbing capabilities.

Figure 4A:
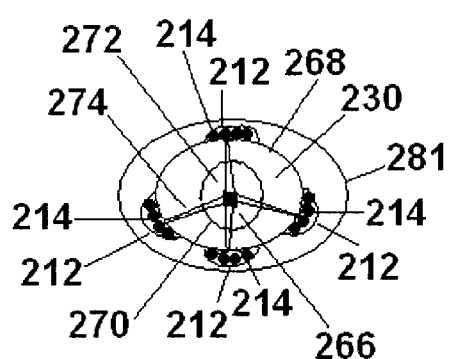
FIG. 4A is a schematic view of another embodiment of an orally administrable implement according to the invention, where the containers are in the first dimension for encapsulation in a capsule of the present invention.
Figure 4B:
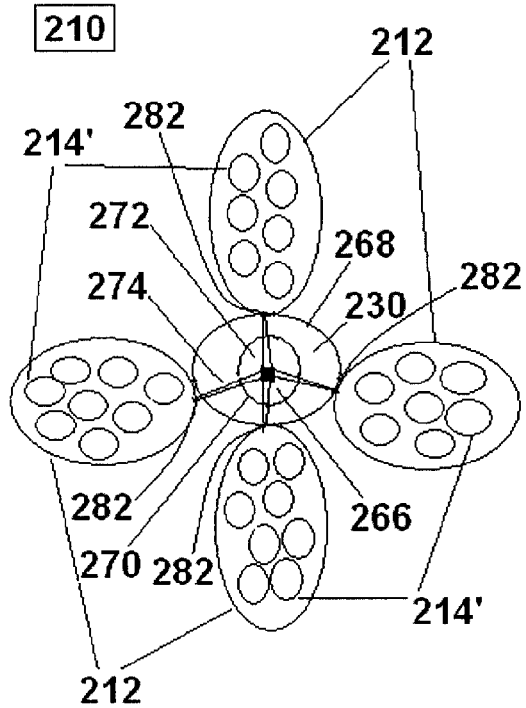
FIG. 4B is a schematic view of the orally administrable implement of FIG. 4A where the containers are in the expanded second dimension.

FIGS. 4A and 4B illustrate another embodiment of an orally administrable implement of the present invention, referred to generally as 210, which is shown in FIG. 4A in its original folded, compact, state and contained in a shell 281, and shown in its expanded state in FIG. 4B. In this embodiment, implement 210 includes a carrier 230 having an outer surface 268 and an inner surface 270, with the inner surface 270 forming an internal cavity 272. Clusters 214 comprising a swellable material are carried in a plurality of containers 212 that are each releasably coupled to the carrier 230 by at least one coupler, shown here as surgical suture 274. The release of the containers 212 relies on the reduction of the tensile strength of the absorbable surgical suture 274. Desirably, suture 274 is arranged so as to maximize coverage of carrier 230 with containers 212.

In the embodiment illustrated in FIGS. 4A and 4B, suture 274 can be threaded through internal cavity 272 of the carrier to form a closed loop so that at least one segment of suture 274 is located within the internal cavity 272. Double-threaded suture 274 can enter carrier 230 at a single location 282 for each sac, and can be knotted with a joint knot 266 contained within the internal cavity 272 of the carrier 230. Of course, if desired, more than one entry location per container can also be used. The sutures connecting each individual container may or may not be of same long-term tensile decay characteristics, so that full or partial disintegration of the implement 210 is achieved. In addition to the joint knot 266 holding the suture knots, the internal cavity 272 may or may not host a microelectronic feedback-providing mechanism registering the exact moment of disintegration, as will be discussed below.

In the embodiment illustrated in FIGS. 4A AND 4B, swellable clusters 214/214' are made from any swellable material, which can include any material that can expand when in contact with aqueous solutions, and can include, but are not limited to, natural clays (for example, which is not meant to be limiting, Bentonite), microcrystalline hydrogels, polyolefins, polyvinyl alcohol, poly(ethyloxazoline), polyvinylacetate-polyvinylalcohol copolymers, poly(2-hydroxyethylacrylate), poly(2-hydroxyethylmethacrylate), polyacrylic acid, and copolymers thereof, polysaccharides, water soluble proteins, polynucleic acids, or a combination thereof. Clusters 214/214' can be made, if desired, of polyacrylic acid and a crosslinker by solution or suspension polymerization, using the type and quantity of crosslinker to control the swelling capacity and the gel modulus. The synthesis and use of such swellable clusters have been previously described in the following references, incorporated herein by reference: (1) Buchholz and Peppas, Superabsorbent Polymers, ACS Symposium Series, 1994; (2) Buchholz and Graham, Modern Superabsorbent Polymer Technology, John Wiley & Sons, 1998; and (3) Biocompatible/Biodegradable Materials (Tutorial). Sigma-Aldrich, 2005, available online at: http://www.siqmaaldrich.com/Area of Interest/Chemistry/Materials Science/BiocompatibleBiodegradable/Tutorial.html.

Containers 212 can be made of a biodegradable expandable permeable liner (for example, absorbable medical gauze). The permeable liner should be able to allow aqueous solutions to enter containers 212 and contact swellable clusters 214 to allow for their expansion (shown in expanded or swelled form in FIG. 4B as 214'). In one embodiment, containers 212 can be made from natural cellulose fiber or specialty fiber through spun laced process, spun-bonded polypropylene or absorbable haemostatic oxidised regenerated cellulose (commercially available under the name Curacel™), and are initially folded, containing the non-expanded clusters. It may be desirable that the material used to construct containers 212 be expandable or stretchable, so as to concurrently expand with the swelling of the clusters 214. As a safety feature, containers 212 may be made of biodegradable material, so as to allow for biodegradation after several days or weeks. Moreover, suture 274 is also made of an absorbable biocompatible material, which can include, but are not limited to polycaprolactone, polyglycolide, polylactide, or combinations thereof (commercially available under the names Selecture PLL™ and Selecture VEH™ by Schering-Plough Animal Health Corporation), or the like, each of which is absorbable and has specific tensile strength decaying characteristics that are not necessarily the same. Thus, if sutures of different tensile strength decaying characteristics are used, gradual partial disintegration of the implement 210 can result. It is preferable that sutures 274 to be capable of withstanding the maximum peristaltic force present in the stomach to prevent release of containers 212 before the said suture biodegrades sufficiently so that the decoupling takes place.

It is understood that other couplers could be used to couple the containers 212 to carrier 230. Couplers can be decoupled by a variety of means known in the art. For example, decoupling of containers includes but is not limited to the natural biodegradation of the holding suture, or of the container holding the clusters itself, or of a combination thereof. Once suture/s 274 is/are sufficiently biodegraded so that they are disrupted, containers 212 can become separated from the orally administrable implement 210.

Carrier 230 can be made of a wide variety of different materials, which can include, but are not limited to, electrically non-conductive silicon and other biocompatible materials such as composite acrylics. The carrier 230 can adopt a wide variety of different shapes. For example, which is not meant to be limiting, carrier 230 can adopt a sphere shape, a cylinder shape, a pyramid shape, a cube shape or combinations thereof. Preferably, the carrier includes one or more sealed compartments, e.g., internal cavity 272, which may further house electronics (see FIG. 7). The electronics can be insulated and may be further encapsulated within the internal cavity of the carrier using electrically non-conductive silicon and other biocompatible materials such as composite acrylics.

As previously mentioned, in the embodiment illustrated in FIGS. 4A and 4B, when the containers 212 are in the compact first dimension, orally administrable implement 210 can be contained within shell 281 to facilitate oral administration. Shell 281 can be made of a variety of different materials, which can include, but are not limited to, pH-sensitive materials that will only dissolve under certain conditions, for example, the pH of the stomach. The material used to make the shell can be the same material, for example, gelatine or cellulose, used to make pharmaceutical capsules known in the art. Various sizes of shells can be used, as long as they are swallowable by the patient.

Figure 5:
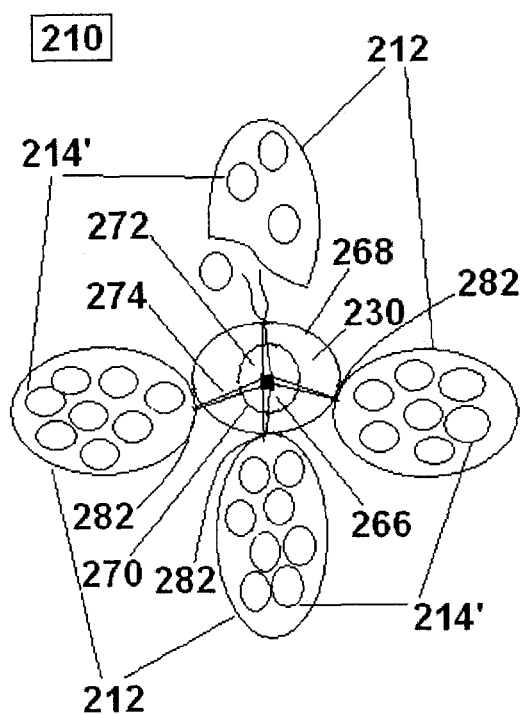
FIG. 5 is a schematic view of an embodiment of the orally administrable implement of the present invention, where the coupler is an absorbable surgical suture that is interrupted at a single point due to its decaying tensile strength.

FIG. 5 shows one embodiment of the present invention where containers 212 are biodegradable. In this embodiment, container 212 separates from coupler 274 when container 212 starts to disintegrate at the point of attachment 282 of coupler 274 to container 212. Once container 212 detaches, swelled clusters 214' are released into the stomach.

Figure 6:
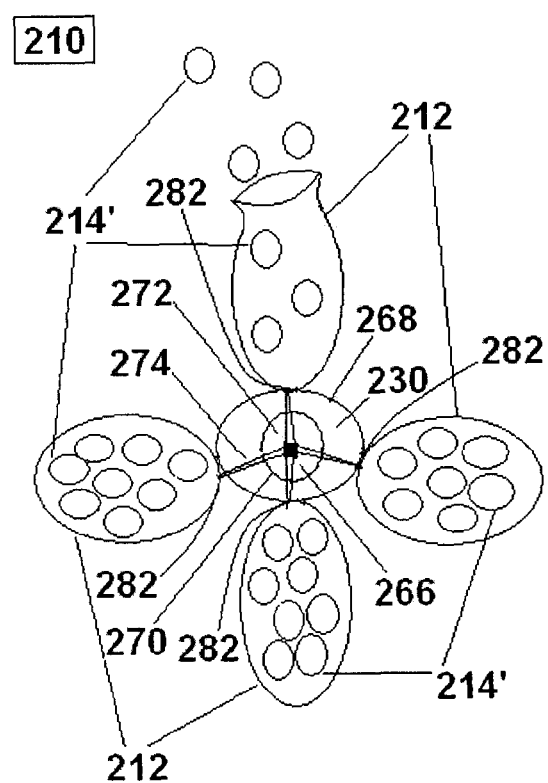
FIG. 6 is a schematic view of an embodiment of the orally administrable implement of the present invention, where the container holding the swelled swellable clusters disintegrates to release the swelled swellable clusters.

FIG. 6 shows another embodiment of the present invention where containers 212 are biodegradable. In this embodiment, container 212 does not separate from coupler 274. Instead, container 212 starts to disintegrate at a point opposite from the point of attachment 282 of coupler 274 to container 212. Once container 212 starts to disintegrate, swelled clusters 214' are released into the stomach.

Figure 7:
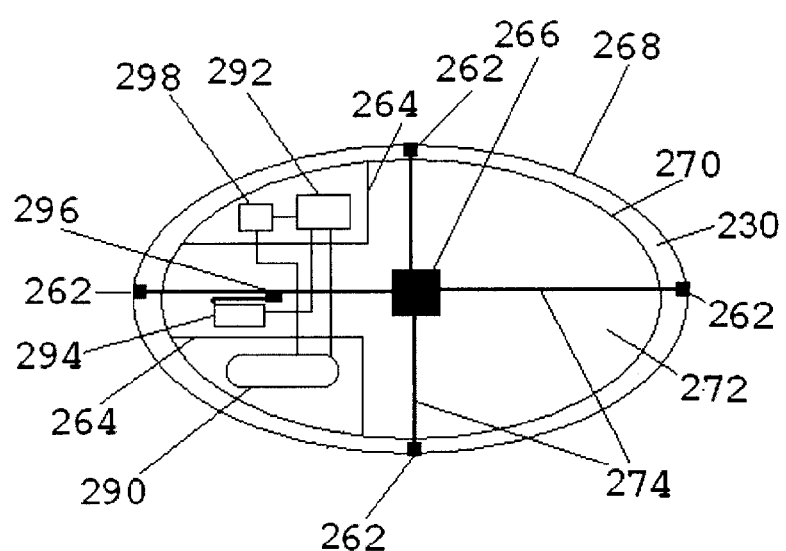
FIG. 7 is a schematic view of a microelectronic system used to provide feedback about the exact moment of disintegration.

FIG. 7 illustrates, in a schematic view, one possible mechanism for providing microelectronic feedback information from an embodiment of an orally administrable implement of the present invention to the external world about the exact moment of disintegration of the implement. FIG. 7 shows carrier 230 having an outer surface 268 and an inner surface 270, with the inner surface 270 forming an internal cavity 272. Housed within internal cavity 272 is battery 290, which supplies microcontroller 292 through microswitch 294 which has lever 296 that is connected to coupler (suture) 274 in such manner that when the device is intact, the microelectronic components are not turned on. Once the tensile strength of suture 274 diminishes and it becomes loose, the microswitch 294 flips back, turning on the microcontroller 292, which controls a radio-frequency (RF) transmitter 298, sending a message to the external world that disintegration of the device has occurred. Suture 274 is threaded through openings in the carrier 230, which are sealed by biocompatible silicon sealant 262.

Figures 8A, 8B:
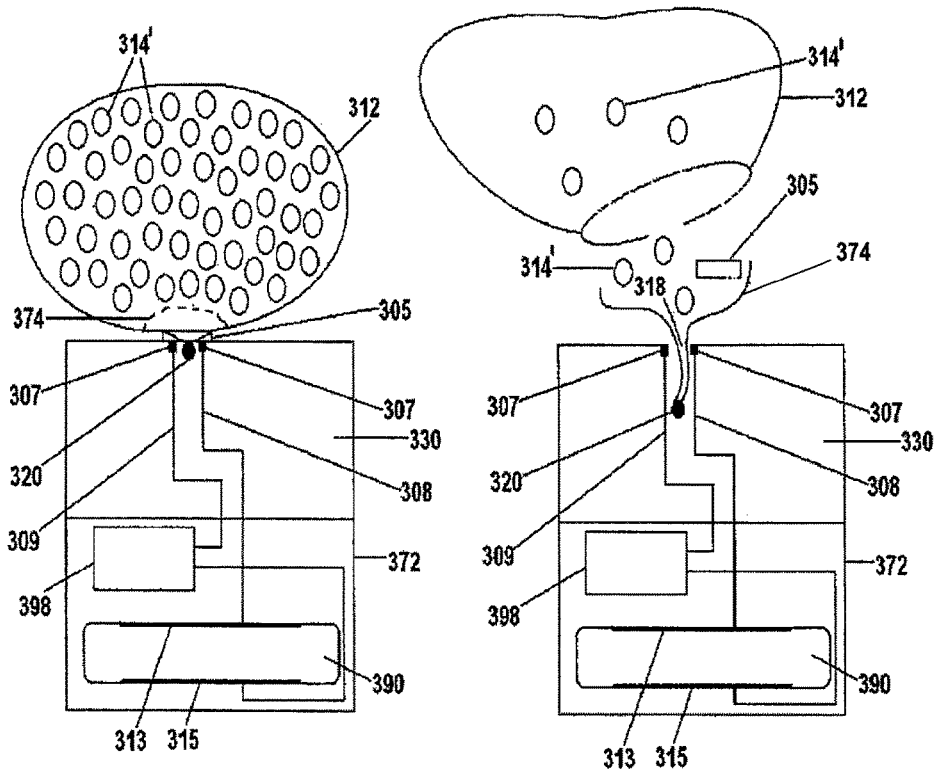
FIG. 8A and FIG. 8B are schematic views of another microelectronic system used to provide feedback about the exact moment of disintegration, showing the intact and disintegrated system, respectively.

FIGS. 8A and 8B illustrate, in a schematic view, another possible mechanism for providing microelectronic feedback information from another embodiment of an orally administrable implement of the present invention to the external world about the exact moment of disintegration of the said implement. Clusters 314' comprising swellable material (for example, Aquagel™ by Akina Inc., West Lafayette, Ind.) are stored in an absorbable container 312 (for example, made of Curacel CuraMedical, Zwanenburg, The Netherlands, or Safil™ Mesh Bag, B. Braun, Melsungen, Gernany), which is kept closed and attached to a carrier 330 by absorbable surgical suture 374 (for example, 5.0 PDS II or 5.0 Vicryl™ by Ethicon, Cornelia, Ga.). The suture 374 is knotted inside the carrier 330 with a knot 320. The suture 374 enters the carrier 330 through a silicon cap 305, which seals the carrier 330 when the implement is held together. Included inside carrier 330 is a sealed compartment, internal cavity 372, which hosts a radio-frequency transmitter 398 and a battery 390. The positive terminal 313 of the battery 390 is connected to a wire 308 terminating at the vicinity of the opening 318 sealed by the silicon cap 305 with an electrical terminal 307. Another such terminal is located close to the first, again in the vicinity of the opening 318, and an electrical wire 309 connects it to the positive terminal of the radio-frequency transmitter 398. The negative terminal 315 of the battery 390 is connected directly to the negative terminal of the radio-frequency transmitter 398. When the surgical suture 374 holding the implement together disintegrates, the silicon cap 305 keeping the carrier 330 sealed detaches, and the inside of the carrier 330 gets moisturized by gastric ionic juices, thus short-circuiting the wires 308 and 309. The electric circuit supplying the radio-frequency transmitter 398 is now closed, and the radio-frequency transmitter emits a signal to the external world, informing that the disintegration of the device has taken place. The wires 308 and 309 are kept very close together, so even small moisturizing in the carrier 330 after the sealing cap 305 detaches is sufficient to create a short circuit, thus connecting the radio-frequency transmitter 398 to the battery 390 and to broadcast a signal denoting the exact moment of disintegration. The miniature sealing cap 305 can be made of biocompatible silicon.

Carrier 330 can be made of a wide variety of different materials, which can include, but are not limited to electrically non-conductive silicon and other biocompatible materials such as composite acrylics. The carrier 330 can adopt a wide variety of different shapes. For example, which is not meant to be limiting, carrier 330 can adopt a sphere shape, a cylinder shape, a pyramid shape, a cube shape or combinations thereof. Preferably, the carrier includes one or more sealed compartments, e.g., internal cavity 372, as shown in FIGS. 8A and 8B, which house the necessary electronics. The electronics can be insulated and may be further encapsulated within the internal cavity of the carrier using electrically non-conductive silicon and other biocompatible materials such as composite acrylics.

As discussed above, clusters of molecules 314' can include any material that can expand when in contact with aqueous solutions, and can include, but are not limited to, natural clays (for example, which is not meant to be limiting, Bentonite), microcrystalline hydrogels, polyolefins, polyvinyl alcohol, poly(ethyloxazoline), polyvinylacetate-polyvinylalcohol copolymers, poly(2-hydroxyethylacrylate), poly (2-hydroxyethylmethacrylate), polyacrylic acid, and copolymers thereof, polysaccharides, water soluble proteins, polynucleic acids, or a combination thereof. Moreover, they can be prepared using a variety of different methods, also discussed above.

Figure 9A:
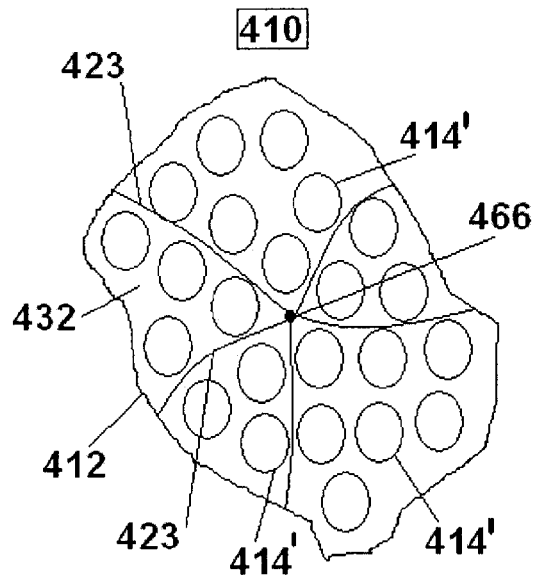
FIG. 9A is a schematic view of an embodiment of an orally administrable implement of the present invention where the container is made from closely knitted permeable absorbable mesh that is held together by radial fibers.
Figure 9B:
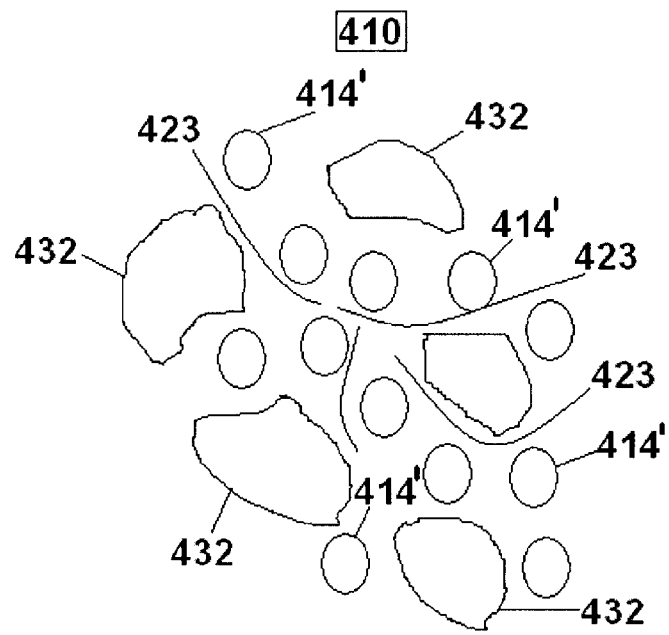
FIG. 9B is a schematic view of the embodiment of the orally administrable implement of FIG. 9A where the radial fibers begin to disintegrate thereby causing the volume of the container to collapse, thus compromising the integrity of the container and releasing the swelled swellable clusters as a result of the gastric peristaltic forces taking the container apart.

FIGS. 9A and 9B illustrate schematically another embodiment of an orally administrable implement of the present invention. In this embodiment, implement 410 comprises container 412 made from permeable absorbable mesh such as Vicryl™ Knitted Mesh by Ethicon, Curacel™ by CureMedical, or Safil™ Mesh by B Braun. The container 412 is held together by radial fibers 423 made from absorbable surgical suture such as Vicryl™, PDS II™ (Ethicon), cat gut, regenerated cellulose or Monosyn™ (B Braun). Inside the container 412 are located the absorbent molecule clusters 414' which upon expansion or swelling in the gastric juice become spherical bodies not exceeding about 1 cm, preferably, not exceeding about 0.5 to about 0.6 cm in diameter. The clusters 414' can be made of various substances, for example, appropriately cross-linked poly(acrylic acid) or poly(2-hydroxyethyl methacrylate). They are of size not permitting their exit from the carrier when dry (unswelled), and not exceeding 1 cm when swelled in the presence of gastric fluid. In addition, preferably the clusters cannot grow any bigger in the small intestine and the colon to prevent them from causing intestinal obstruction.

FIG. 9B represents the released pieces 432 of the absorbable mesh, each of which is of size precluding the possibility of creating obstruction in the small intestine. The weakened disintegrating radial fibers 423 cannot hold the structure together, the gastric peristaltic forces take it apart, and the carrier pieces 432, and the polymer clusters 414' are released in the stomach, so that they can be propelled out of the body by natural peristalsis in a harmless fashion. Thus, the artificially created temporary gastric bezoar ceases to exist.

Figure 10A:
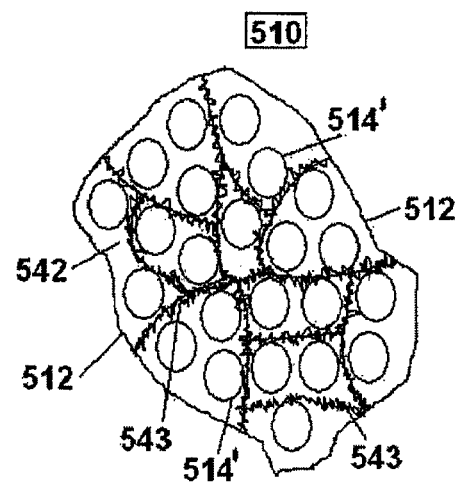
FIG. 10A is a schematic view of an embodiment of an orally administrable implement of the present invention where the container is made from a plurality of sections sutured together with biodegradable fibers.
Figure 10B:
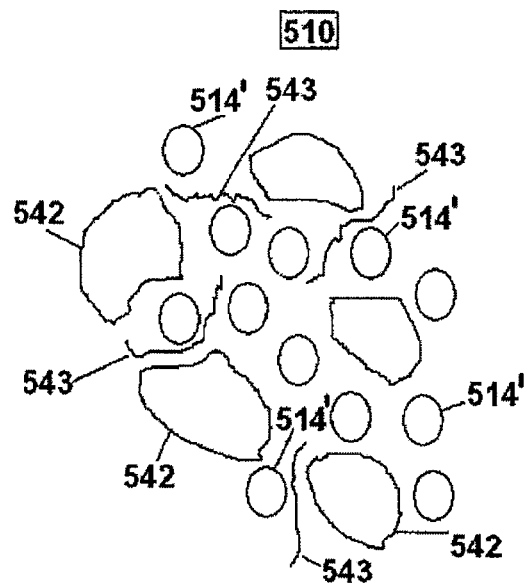
FIG. 10B is a schematic view of the embodiment of the orally administrable implement of FIG. 10A where the sutures begin to disintegrate thereby compromising the integrity of the container and releasing the fibers.

FIGS. 10A and 10B illustrate schematically another embodiment of an orally administrable implement of the present invention. In this embodiment, implement 510 comprises container 512 made from a plurality of sections 542 made from permeable absorbable mesh such as Vicryl™ Knitted Mesh by Ethicon, Curacel™ by CuraMedical, or Safil™ Mesh by B Braun. The container 512 is assembled with several pieces of the said mesh 542, precisely and securely stitched together by absorbable surgical suture 543 such as Vicryl™ PDS II™ (Ethicon) or Monosyn™ (B Braun). These surgical sutures 543 act as coupling members and are utilized to hold the container together and help maintaining its volume upon digestion. Inside the container 512 are located clusters 514' comprising swellable material, which upon expansion in the gastric fluid become spherical bodies not exceeding 1 cm, preferably not exceeding about 1 cm in diameter. The clusters 514' can be made of various substances, for example, appropriately cross-linked poly (acrylic acid) or poly(2-hydroxyethyl methacrylate). They are of size not permitting their exit from the carrier when dry, and preferably not exceeding about 0.5 to about 0.6 cm in diameter when swelled in gastric fluid. In addition, they cannot grow any bigger in the small intestine and the colon to prevent them causing intestinal obstruction. FIG. 10B shows the structure after it has started its disintegration.

Figure 11A:
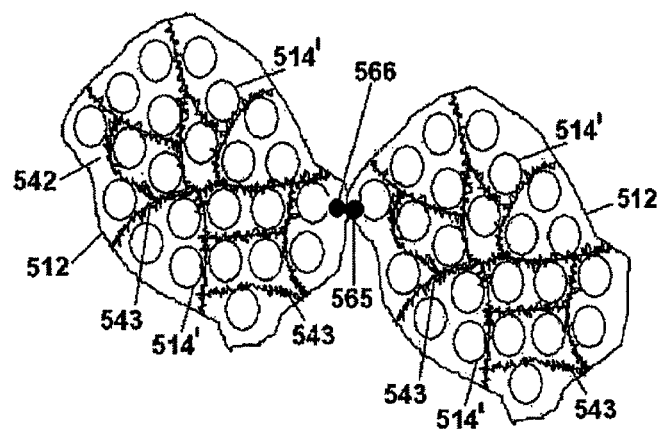
FIG. 11A is a schematic of an embodiment of two orally administrable implements of the present invention wherein each container is made from a plurality of sections held together with biodegradable fibers and each container having a magnet contained therein.
Figure 11B:
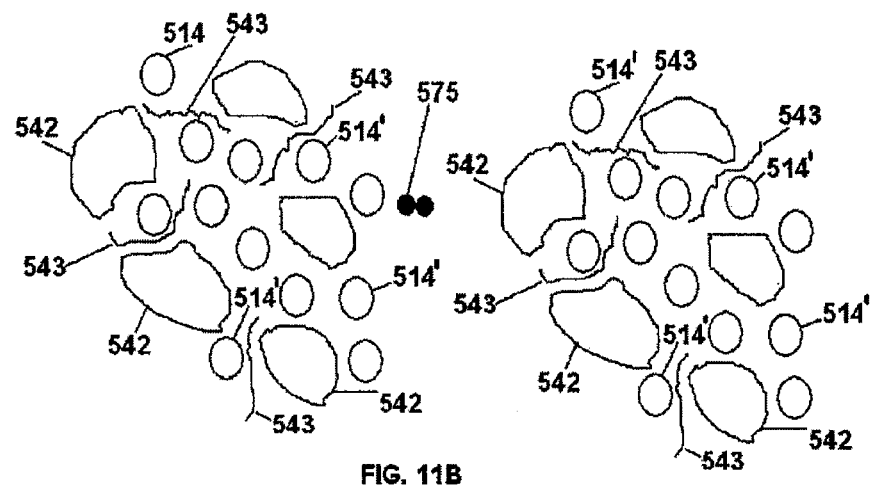
FIG. 11B is a schematic view of the embodiment of the two orally administrable implements of FIG. 11A where the fibers begin to disintegrate, the containers fall apart, and the swelled swellable clusters are released.

FIGS. 11A and 11B depict another embodiment of an orally administrable implement of the present invention. In this embodiment, two containers 512 are essentially as shown in FIG. 10A except each container 512 further comprises a spherical rare Earth magnet 565, covered by thin biocompatible silicone cover 566. When each container 512 is individually ingested in a pre-determined sequence, and upon expansion in the stomach, the two rare Earth magnets 565 contained in each container 512 attract each other and two temporary bezoars form a larger volume. FIG. 11B represents the released pieces 542 of the absorbable mesh in both temporary bezoars, each of which is of size precluding the possibility of creating obstruction in the small intestine. The weakened disintegrating sutures 543 cannot hold the structure together, and the mesh pieces 542, the sutures 543, the swellable clusters 514' and the still coupled magnets 575 are released in the stomach, so that they can be propelled out of the body by natural peristalsis in a harmless fashion. The two small rare Earth magnets 575 remain bonded together, but are of size that cannot create any intestinal obstruction. Thus, the artificially created temporary gastric bezoar ceases to exist and all of its components exit the stomach and the gastrointestinal tract without creating obstruction.

Figures 12A, 12B, 12C:
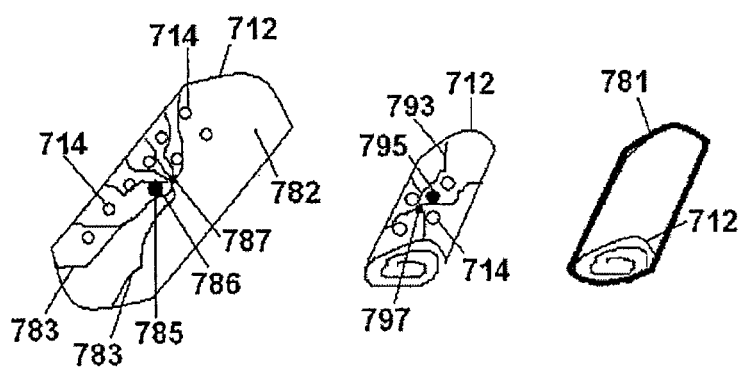
FIGS. 12A, 12B and 12C represent a schematic drawing of a possible way to vacuum-packing an orally administrable implement of the present invention before positioning it in an ingestible capsule.

FIGS. 12A, 12B and 12C represent a schematic drawing of a possible way to vacuum-packing an orally administrable implement of the present invention before positioning it in an ingestible capsule, so that no or minimal volume space in the said capsule is left non-utilized. In FIG. 12A the container 712 is planary situated and is made from absorbable permeable knitted or woven mesh 782, which is vacuum-compressed, while containing inside fibers 783 made of absorbable surgical suture and tied together in a knot 787, dry superabsorbent polymer clusters 714, and a miniature rare Earth permanent magnet 785, covered with a thin biocompatible layer 786. In FIG. 12B, the container 712 made of absorbable permeable knitted or woven mesh 792 is tightly folded and in it tightly compressed together are the fibers 793 made of absorbable surgical suture and tied together in a knot 797, the dry superabsorbent polymer clusters 714, and the miniature rare Earth permanent magnet 795. FIG. 12C depicts the folded carrier 712 as it fits precisely and without leaving unutilized volume in a stomach-targeted rapidly absorbable ingestible capsule 781, for example AAA R&D capsule by Capsugel™, Pfizer, New York, N.Y.

Figure 13A:
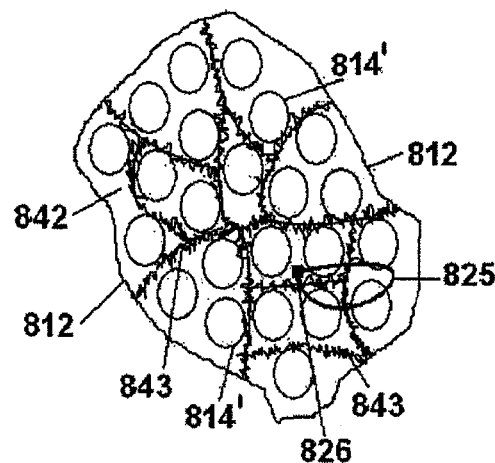
FIG. 13A is a schematic view of an embodiment of an orally administrable implement of the present invention where the container is made from a plurality of sections held together with biodegradable fibers and the container further houses a radio-frequency identification (RFID) tag.

FIG. 13A represents a container 812 made from permeable absorbable mesh such as Vicryl™ Knitted Mesh by Ethicon, Curacel™ by CuraMedical, or Safil™ Mesh by B Braun. The container 812 is assembled with separate sections 842 of the mesh, precisely and securely stitched together by absorbable surgical suture 843 such as Vicryl™, PDS II™ (Ethicon) or Monosyn™ (B Braun). Inside the container 812 are located the swellable clusters 814' which upon expansion in the gastric juice become spherical bodies not exceeding about 0.5 to about 0.6 cm in diameter. The swellable clusters 814' can be made of various substances, for example, appropriately cross-linked poly(acrylic acid) or poly(2-hydroxyethyl methacrylate). They are of a size not permitting their exit from the container when dry, and not exceeding 0.5-0.6 cm when swollen in gastric acid. In addition, they cannot grow any bigger in the small intestine and the colon to prevent them causing intestinal obstruction. The container 812 further contains a radio-frequency identification (RFID) tag 825 to determine the exact location of the device within the gastrointestinal (GI) tract using an external RFID reader.

Figure 13B:
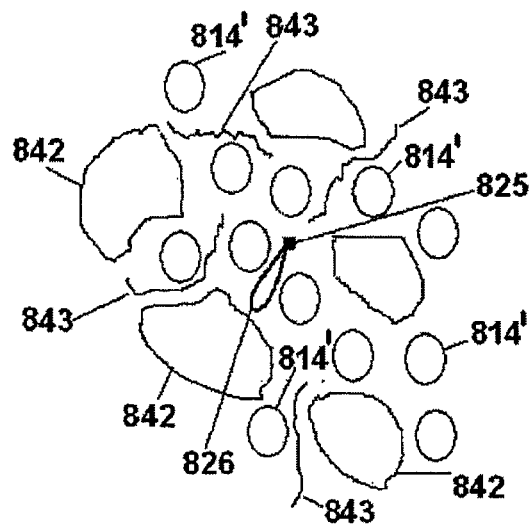
FIG. 13B is a schematic view of the embodiment of the orally administrable implement of FIG. 13A where the fibers begin to disintegrate thereby compromising the integrity of the container.

The RFID tag 825 is contained within the volume of the container 812 and has an antenna 826 attached to it. The antenna 826 is folded in the non-expanded capsule, and unfolds to facilitate the communication of the RFID tag 825 with an external RFID reader 827 positioned in the vicinity of the abdominal area of the patient. FIG. 13B represents the released sections 842 of the absorbable mesh, each of which is of size precluding the possibility of creating obstruction in the small intestine. The weakened disintegrating sutures 843 cannot hold the structure together, and the container sections 842, the RFID tag 825, the antenna 826, and the clusters 814 are released in the stomach, so that they can be propelled out of the body by natural peristalsis in a harmless fashion. Thus, the artificially created temporary gastric bezoar ceases to exist. The external RFID reader 827 records the changed position of the internal RFID tag 825 after the disintegration of the internal temporary gastric bezoar.

Figure 14:
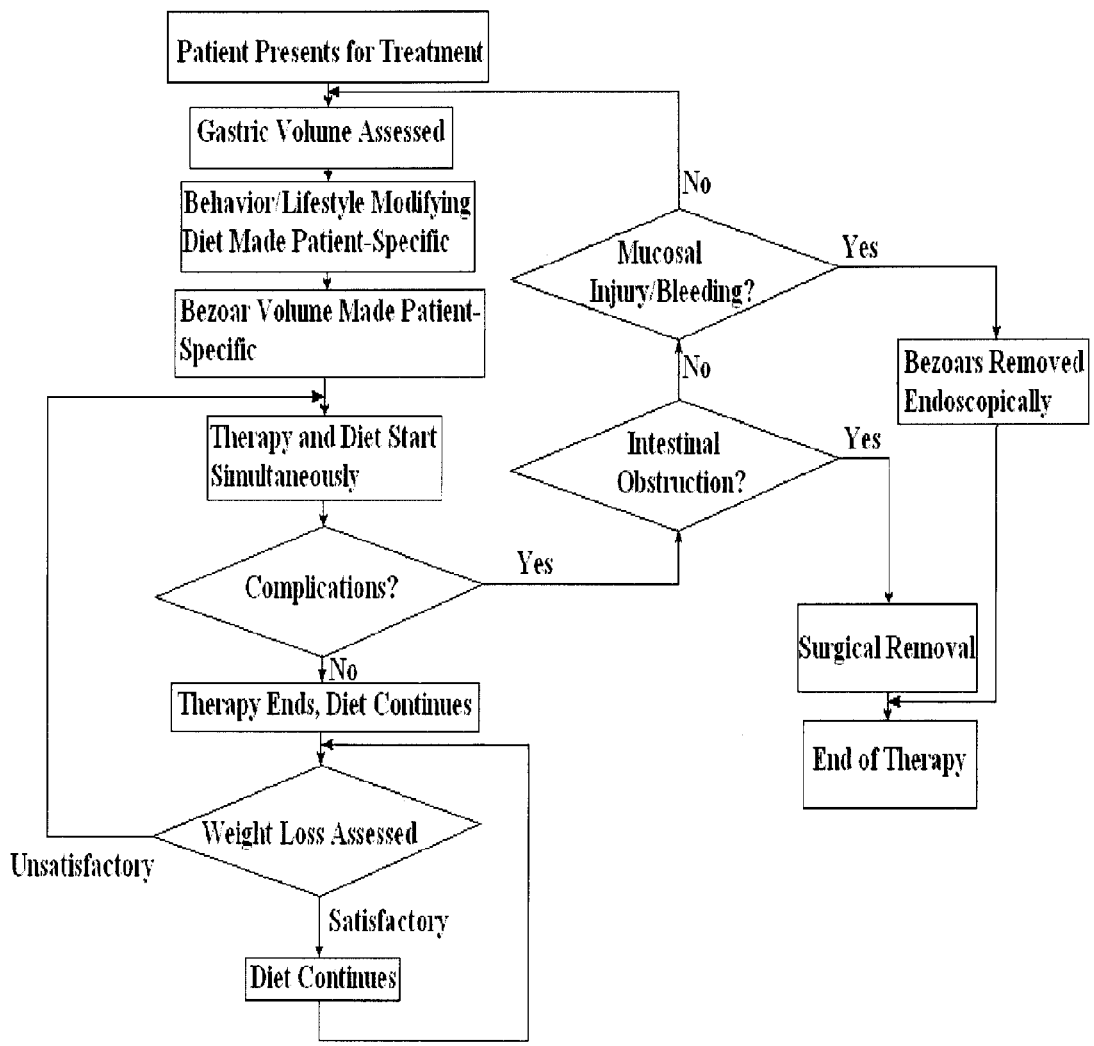
FIG. 14 represents a block-diagram of a possible administration schedule of an orally administrable implement of the present invention.

FIG. 14 represents a block-diagram of a possible administration schedule that can be in conjunction with an appropriately designed patient-specific behavior/lifestyle modifying diet. The figure also outlines how various possible complications can be handled in the course of the therapy.

Figure 15A:
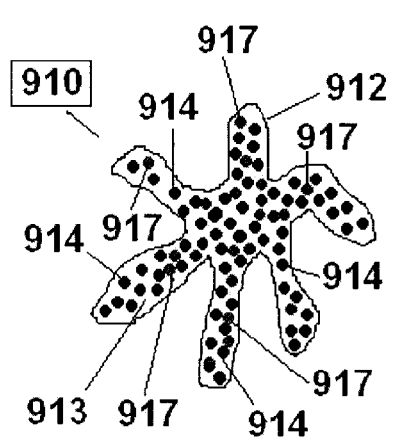
FIG. 15A is a schematic view of one embodiment of an unexpanded orally administrable implement according to the invention where the container has therein both swellable clusters and substance-absorbing clusters.
Figure 15B:
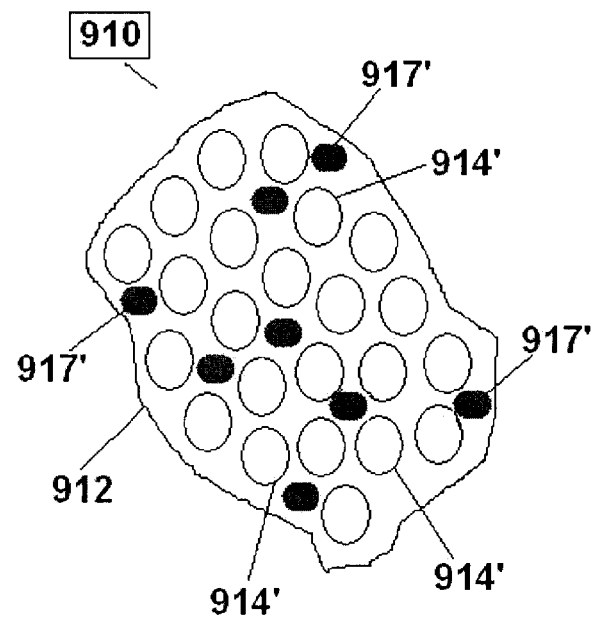
FIG. 15B is a schematic view of the orally administrable implement of FIG. 15A in the expanded second dimension as a result of both the swellable clusters and the substance-absorbing clusters swelling.
Figure 15C:
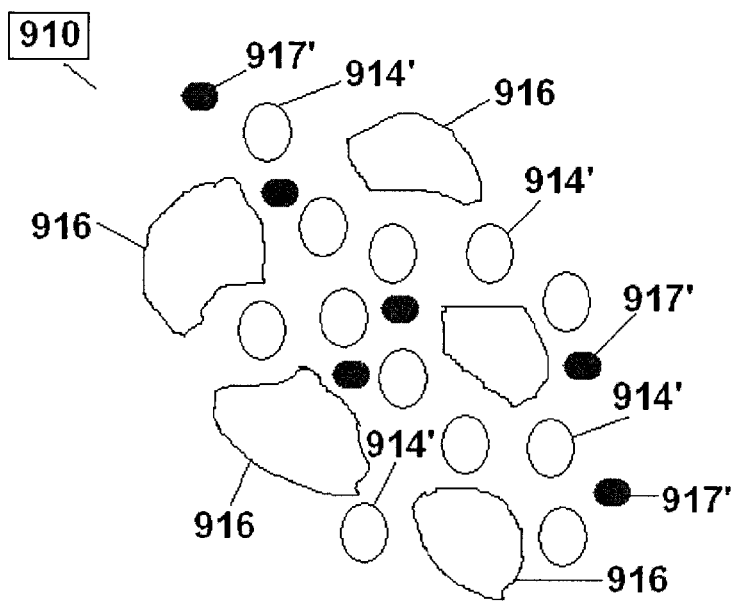
FIG. 15C is a schematic view of the orally administrable implement of FIG. 15B where the container is made of a biodegradable material for releasing the swelled swellable clusters and the substance-absorbing clusters.

In another embodiment of the present invention, illustrated in FIGS. 15A, 15B and 15C, the orally administrable implement, referred to generally as 910, comprises a container 912, shown here in a folded, compact, first dimension. In this embodiment, container 912 is made from a biodegradable material that allows for the passage of fluid into its interior 913, for example, a permeable biodegradable mesh such as Vicryl™ Knitted Mesh by Ethicon, Curacel™ by CureMedical, or Safil™ Mesh by B Braun. Further contained in the interior 913 of container 912 is a plurality of clusters 914 comprising a swellable material, whereby each swellable cluster is capable of swelling when contacted with fluid such as gastric fluid found in the stomach. For example, swellable clusters 914 can comprise Aquagel™ by Akina Inc., West Lafayette, Ind. In FIG. 1A, the swellable clusters 914 are shown prior to contact with fluid, i.e., in their non-swelled form.

Orally administrable implement 912 further comprises a plurality of clusters comprising a substance-absorbing material (substance-absorbing clusters 917) contained within the container 912 and capable of absorbing targeted substance or substances present in the gastric fluid. For example, which is not meant to be limiting, the substance-absorbing clusters 917 may be lipid-absorbing and may comprise chitosan, or any other material known to have lipid-absorbing properties.

FIG. 15B shows implement 910 of FIG. 15A in its expanded form, after it has been delivered into the stomach and gastric fluid has been allowed to contact it. Container 912 is now shown in its second, expanded dimension, such that the implement 910 can no longer exit the stomach through the pylorus. The swellable clusters 914' are now shown in their swelled state due to the gastric fluid seeping through the container 912. The swelling of clusters 914' causes container 912 to expand to the second dimension. Preferably, the swelled clusters 914' become spherical bodies not exceeding 1 cm in diameter. The clusters can be made of various substances, for example, appropriately cross-linked poly(acrylic acid) or poly(2-hydroxyethyl methacrylate). Preferably, they are of size not permitting their exit from the carrier when dry, and not exceeding about 0.5 to about 0.6 cm when swollen in gastric fluid. In addition, preferably, they cannot grow any bigger in the small intestine and the colon to prevent them causing intestinal obstruction. The substance-absorbing clusters 917' do not expand to size greater than about 1 cm, preferably, not exceeding about 0.5 to about 0.6 cm after substance absorption, so that they also do not cause intestinal obstruction and can be easily expelled through the pylorus.

The substance-absorbing clusters 917' are retained in the stomach long enough to absorb substance present in the gastric fluid, such as for example lipids, due to being retained in the container 912 and the implement 910 expanding to a size that cannot exit the stomach via the pylorus as a result of the swellable clusters 914' swelling when contacted with gastric fluid.

FIG. 15C represents the released pieces 916 of the container 912 in FIG. 15B once it biodegrades, each piece 916 of which is of size precluding the possibility of creating obstruction in the small intestine. The container pieces 916 along with the swelled clusters 914' and substance-absorbing clusters 917' are released in the stomach, so that they can be propelled out of the body by natural peristalsis in a harmless fashion.

Example 1

Preparation of Swellable Cluster-Filled Containers

To make containers, 10 cm×8 cm pieces of Vicryl™ knitted mesh gauze were folded in two to form hollow cylinders with a diameter of 3 cm and a height of 8 cm. Each folded gauze was sutured on two sides using USB 6.0 Vicryl™ surgical sutures, leaving an open third side. The sutured gauze was then turned inside out so that the sutures are now located ion the inside of the containers.

Two different dry polymer clusters were used in the following example. To form a bezoar of Type 1, about 1.0 to about 1.5 cc of dry polymer clusters comprising swellable polyacrylamide were added to the inside of the container through the open end. The average size of the dry polyacrylamide clusters ranged in size from about 500 micrometers to about 1200 micrometers. To form a bezoar of Type 2, about 1.0 to about 1.5 cc of dry polymer clusters comprising swellable cross-linked polyacrylic acid were added to the inside of the container through the open end. The average size of the dry polyacrylic acid clusters ranged in size from about 150 micrometers to about 850 micrometers. Once the clusters were added to the containers, the open sides of the containers were sutured closed with USB 6.0 Vicryl™ surgical sutures.

The filled containers were then folded, compressed and made to fit into a standard AAA capsule.

Administration of Swellable Cluster-Filled Containers to Two Dogs

Two mongrel dogs (1M, 1F, 25.1 kg and 30.25 kg, respectively) were submitted to 20 days baseline study with the following daily feeding and water intake schedule:
9:00 AM: Administration of 40 mg Pantoprazole orally
9:10-9:30 AM: Access to 300 ml of water and 200 mg of standard canine food (Akana™ Champion Pet Foods, Morinville, Alberta, Canada)
9:30-9:40 AM: Break
9:40-10:40 AM: Access to additional 1 liter of water and 1 kg of the same standard canine food.
The food intake, water intake, bowel movements, pain and behavioral symptoms were monitored and recorded during this 20 day Baseline Period.

Immediately after the Baseline Period, the dogs were administered 10 ingestible capsules (one capsule per day per dog) each containing a 50 cc container (cylindrical sac) designed from Vicryl™ knitted mesh (Ethicon, Summerville, N.J.) of 8 cm height and 3 cm diameter, as described above. The containers were filled with either dry polymer clusters made from polyacrylamide (The Artistic Shop, Pewaukee Wis.) (Type 1 bezoars, which were administered to the male dog) of about 0.5 to about 1.2 mm in diameter or cross-linked polyacrylic acid (Wako Pure Chemical Industries, Osaka, Japan) (Type 2 bezoars, which administered to the female dog) of 0.15 to 0.85 mm in diameter. The encapsulation was in standard gelatin AAA capsules (Capsugel™, Peapak, N.J.). The administration of the capsules took place during the 9:30-9:40 AM break of the regular feeding schedule, modifying the latter as follows:
9:00 AM: Administration of 40 mg Pantoprazole orally to maintain gastric acidity at levels above pH of 3;
9:10-9:30 AM: Access to 300 ml of water and 200 mg of standard canine food.
9:30-9:40 AM: Administration of one ingestible bezoar capsule
9:40-10:40 AM: Access to additional 1 L of water and 1 kg of standard canine food.
The food intake, water intake, bowel movements, pain and behavioral symptoms were monitored and recorded in the same fashion as during the Baseline Period.

The food intake and weight dynamics were averaged for the baseline and the therapy periods, and were compared. In addition, the food intake measurements during the baseline and during therapy were compared for statistically significant differences using a single-tailed two-sampled unequal variance Student T-test.

Except for two vomiting incidents (one in each dog), no other adverse effects were observed. No signs of esophageal or gastrointestinal obstruction were noted in either dog, who were alert, active, and had regular daily bowel movements during the entire duration of the therapy. The male dog expelled two bezoars with bowel movements, a single bezoar was expelled by the female dog. No occult blood in the stools, constipation, or diarrhea were noted in both animals during the baseline or the therapy periods.

The food intake was reduced by 35% in the male dog (Type 1 bezoars) and by 51% in the female dog (Type 2 bezoars). The reduction of the food intake was statistically significant in both animals, with $p<0.05$ for the male dog and $p<0.005$ for the female dog. By the end of the 10-days therapy the male dog lost 1.2 kg, and the female dog lost 1.5 kg in weight (4.7% and 4.9%, respectively). Examination of the expelled bezoars in the stools revealed that the superabsorbent polymer clusters swelled to about 0.5-0.7 cm diameter, were expellable through the pylorus upon the disintegration of the sac carrier, and were sufficiently soft to prevent gastrointestinal obstruction. Combined with the permeable nature of the container, this temporary bezoar design appears to be a safe and reliable way of reducing gastric volume and regulating food intake for the treatment of obesity.

Example 2

Swellable Cluster and Substance-Absorbing Cluster Filled Containers

Chitosan clusters ranging in size from about 200 micron to about 600 micron were manufactured and supplied by Attix Pharmachem, Toronto, ON and served as lipid-absorbing clusters to be included in a 3×8 cm pillow-like permeable container designed from Vicryl knitted mesh (Ethicon), as described above. The containers further contained polyacrylamide clusters ranging in size from about 500 micrometers to about 1200 micrometers, which were supplied by The Artistic Shop, LLC (Pewaukee, Wis.). The containers were filled with about 0.8 cubic centimeters of the chitosan clusters and 0.8 cubic centimeters of the polyacrylamide clusters. The containers were closed as described above with Vicryl™ USP 6.0 surgical suture.

The implement (filled container) was put in a blended mixture of 125 ml of water and 25 ml of sunflower oil. After ½ hour, the oil-water mixture was completely absorbed by the implement. Subsequently, the implement was put in a mini washing machine manufactured by Ningbo Sanxi Electric Co, Ltd, Ningbo, Zhejiang, China. The implement was mixed with some cotton clothing to simulate gastric peristaltic forces in the presence of other food. The mini washing machine was turned on in two 2-hour intervals with a 1 hour break between them. The implement retained its volume, and no visible oil was released by the chitosan clusters.

While the invention has been described in conjunction with the disclosed embodiments, it will be understood that the invention is not intended to be limited to these embodiments. On the contrary, the current protection is intended to cover alternatives, modifications and equivalents, which may be included within the spirit and scope of the invention. Various modifications will remain readily apparent to those skilled in the art.

What is claimed is:

1. An orally administrable implement for expanding in a stomach of an animal, including a mammal, to fill a space in the stomach, comprising:

(a) a fluid-permeable expandable container having a first dimension and being expandable to a second dimension; and (b) a plurality of clusters comprising a swellable material contained within the container and capable of swelling when contacted with a fluid;

whereby when the implement is ingested, the fluid in the stomach enters the container causing the clusters therein to swell and the container to expand from the first dimension to the second dimension;

wherein the container is made from an absorbable woven, knitted, braided or monofilament mesh material.

2. The orally administrable implement as claimed in claim 1, wherein the container, while in the first dimension, is configured for retention in an ingestible capsule.

3. The orally administrable implement as claimed in claim 1, wherein the container is configured to be sufficiently large in the second dimension so as to be retained in the stomach after ingestion.

4. The orally administrable implement as claimed in claim 1, wherein the container is biodegradable over time.

5. The orally administrable implement as claimed in claim 4, whereby when the container biodegrades the clusters are released into the stomach.

6. The orally administrable implement as claimed in claim 1, wherein the clusters are configured to not exceed about 1.0 cm in diameter when swollen.

7. The orally administrable implement as claimed in claim 6, wherein the clusters are configured to not exceed about 0.6 cm in diameter when swollen.

8. The orally administrable implement as claimed in claim 1, wherein the container is made from a fluid-permeable stretchable material.

9. The orally administrable implement as claimed in claim 1, wherein the container is made from a permeable absorbable mesh having radial fibers woven therethrough.

10. The orally administrable implement as claimed in claim 1, further comprising a magnet retained in the container.

11. The orally administrable implement as claimed in claim 1, further comprising at least one active agent, which can be releasably associated with either the container, the clusters of swellable material, or both.

12. The orally administrable implement as claimed in claim 11, the at least one active agent is selected from the group consisting of enzymatic agents, medicinal agents, chemical agents, or combinations thereof.

13. The orally administrable implement as claimed in claim 1, further comprising a radio-frequency identification (RFID) tag.

14. The orally administrable implement as claimed in claim 1, further comprising a radio-frequency transmitter.

15. The orally administrable implement as claimed in claim 1, further comprising a plurality of clusters comprising a substance-absorbing material contained within the container and capable of absorbing the targeted substance present in the stomach.

16. The orally administrable implement as claimed in claim 15, wherein the substance-absorbing material is a lipid-absorbing material.

17. The orally administrable implement as claimed in claim 16, wherein the lipid-absorbing material is lipid-absorbing chitosan fiber, oxidized cellulose fiber, or a combination of both.

18. The orally administrable implement as claimed in claim 1, wherein the container is made from fiber comprising a substance-absorbing material.

19. The orally administrable implement as claimed in claim 18, wherein the substance-absorbing material is a lipid-absorbing material.

20. The orally administrable implement as claimed in claim 19, wherein the lipid-absorbing material is lipid-absorbing chitosan fiber, oxidized cellulose fiber, or a combination of both.

21. The orally administrable implement as claimed in claim 1, wherein the implement is self-administrable in the case of humans or administrable autonomously.

22. An orally administrable implement for expanding in a stomach of an animal, including a mammal, to fill a space in the stomach, comprising:
   (a) a fluid-permeable expandable container having a first dimension and a second dimension; and
   (b) a plurality of clusters comprising a swellable material contained within the container and capable of swelling when contacted with a fluid;
whereby when the implement is ingested, the fluid in the stomach enters the container causing the clusters therein to swell and the container to expand from the first dimension to the second dimension;
   wherein the container comprises a plurality of smaller sections, whereby each section is connected to one another by absorbable fiber to form the container.

23. The orally administrable implement as claimed in claim 22 wherein the container is made from an absorbable woven, knitted, braided or monofilament mesh material.

24. An orally administrable implement for expanding in a stomach of an animal, including a mammal, to fill a space in the stomach, comprising:
   (a) a fluid-permeable expandable container having a first dimension and a second dimension; and
   (b) a plurality of clusters comprising a swellable material contained within the container and capable of swelling when contacted with a fluid;
whereby when the implement is ingested, the fluid in the stomach enters the container causing the clusters therein to swell and the container to expand from the first dimension to the second dimension;
   wherein the swellable material of the clusters is selected from the group consisting of a swelling bentonite, microcrystalline hydrogels, polyolefins and various mixtures thereof.

* * * * *